United States Patent
Onda et al.

[11] Patent Number: 6,020,175
[45] Date of Patent: Feb. 1, 2000

[54] MULTIPLE LAYERED FUNCTIONAL THIN FILMS

[75] Inventors: Mitsuhiko Onda; Yuri Lvov; Katsuhiko Ariga, all of Kurume; Toyoki Kunitake, Fukuoka-ken, all of Japan

[73] Assignee: Japan Science and Technology Corporation, Honcho, Japan

[21] Appl. No.: 08/926,493

[22] Filed: Sep. 10, 1997

[30] Foreign Application Priority Data

Sep. 30, 1996 [JP] Japan ................................. 8-280329

[51] Int. Cl.[7] .......................... C12N 11/00; C12N 11/08; C07K 17/00; C07K 17/08
[52] U.S. Cl. ...................... 435/180; 435/174; 435/176; 435/178; 435/182; 530/402; 530/810; 530/811; 530/813; 530/815; 530/817
[58] Field of Search ..................... 435/174, 176, 435/178, 180, 182; 530/402, 810, 811, 813, 815, 817

[56] References Cited

PUBLICATIONS

Biotechnology and Bioengineering article entitled "Sequential Actions of Glucose Oxidase and Peroxidase in Molecular Films Assembled by Layer–by–Layer Alternate Adsorption" vol. 51, pp. 163–167 (1996).

J.Am. Chem. Soc., vol. 117, No. 22, pp. 6117–6123 (1995) article entitled "Assembly of Multicomponent Protein Films by Means of Electrostatic Layer–by–Layer Adsorption".

*Primary Examiner*—David M. Naff
*Attorney, Agent, or Firm*—Fay, Sharpe, Fagan, Minnich & McKee, LLP

[57] ABSTRACT

Multiple layered functional thin films fixed on a solid support are provided which comprise multiple layers of functional molecules (such as enzymes and other proteins, pigments and dyes) admixed with polymer ions in combination with multiple layers of polymer ions without the functional molecules. The films are prepared by immersing a solid support having an electric charge in an admixed polymer ion-functional molecule solution having a net electric charge opposite to that of the solid support followed by immersing the solid support in a polymer ion solution having a net electric charge opposite to that of the admixed polymer ion-functional molecule solution, and repeating at least once the immersings of the solid support in the solutions. Alternatively, the films are prepared by immersing the solid support in a polymer ion solution having a net electric charge opposite to that of the solid support followed by immersing the solid support in an admixed polymer ion-functional molecule solution having a net electric charge opposite to that of the polymer ion solution, and repeating at least once the immersings of the solid support in the solutions.

24 Claims, 7 Drawing Sheets

MULTIPLE LAYERED FUNCTIONAL THIN FILMS

FIELD OF INVENTION

The present invention relates to a functional thin film and a method of making the same, more particularly, to the preparation of a novel ultrathin film, i.e. a thin film regulated at a molecular level by the utilization of the alternate layer-by-layer method.

BACKGROUND OF THE INVENTION

Most biological reactions proceed through highly efficient and selective physical and chemical processes in which proteins such as enzymes or functional pigment molecules work singly or in a cooperative or sequential manner. In order to artificially mimic such functions for developing novel molecular devices such as enzyme reactors, biosensors or luminescent elements, it is necessary to build up a structure or assembly in which functional molecules are layered in a desired sequence. Generally, functional molecules can be layered onto a solid support by one of the following methods: (i) the LB method in which a thin film developed on the surface of a liquid is transferred onto a suppoirt, (ii) the monolayer adsorption method by which functional molecules are fixed directly on a solid support, and (iii) the alternate layer-by-layer method for fixing functional molecules through adsorption alternately with other molecular components.

The LB method is known as a method for preparing a thin film in which the molecular layers are arranged in a desired order with a precision of molecular level. The method comprises dissolving an amphiphilic substance such as a lipid in an organic solvent, spreading a monolayer on an aqueous surface and transferring the monolayer onto a solid substrate, thereby forming a thin film with a desired thickness by controlling the order of the layers. This method suffers from a restriction that it is only applicable to water-insoluble substances having properties similar to surfactants, since the subject substance must be developed on an aqueous surface as a monolayer. In addition, the LB method has a drawback in that it has a poor productibility and requires a device which is expensive and not easy to handle.

The monolayer adsorption method is to fix molecules dissolved in a solution, onto a solid support as a monolayer taking advantage of a strong interaction such as that between silanol and glass or thiol and gold. This method is advantageous in that a water-soluble substance can be employed. It has additional merits that the resultant film is resistant to external actions because of the strong interaction between the solid support and the monolayer and that the fixation can be made regardless of the shape of the solid support. However, the method has a fatal drawback in that chemical reactions with specific functional groups are indispensable for the preparation of a multi-layered structure and thus the substances usable are restricted to those having the specific functional groups which will interact with the support material.

The alternate layer-by-layer method is to prepare a thin film through alternate adsorption of oppositely-charged substances which may be selected in combination from among organic polymer ions, inorganic polymer ions, proteins and the like. The principle of this layering method is as follows: If there is immersed in a solution of polymer ions a solid support whose surface electric charge is opposite to that of the polymer ions, the polymer ions are adsorbed onto the support due to electrostatic interaction. This results in the neutralization of the surface charge of the support by the polymer ions and then the generation of new electric charge due to overadsorption of the polymer ions. Thus, if the resultant assembly is immersed in a solution of a substance having an electric charge opposite to that of polymer ions, for example, in an aqueous solution of a protein, another new electric charge is generated on the surface due to the charge neutralization and the overadsorption. Repetition of this process will enable alternate layering of such substances as polymer ions and proteins in a desired order and substantially in an indefinite manner. The extent of the overadsorption in each step is limited by the charge saturation and thus a limited amount of the polymer ions are fixed on the surface in each step. This method is advantageously carried out in a simple manner without need for any sophisticated devices. The method is also meritorious in that it is suitable for use in the fixation of easily denaturable molecules such as proteins, since a solution of such substance can be directly employed.

However, the alternate layer-by-layer method is not applicable to the preparation of an ulttrathin film composed of non-flexible (rigid) functional molecules, wherein a non-flexible or rigid functional molecule can be defined as a functional molecule incapable of flexibly changing its conformations (special arirangements of atoms in the molecule) in compliance with the fixed electric charge of the surface onto which the molecule is to be adsorbed. For example, this method is not always useful in the preparation of an ultrathin film by layering functional molecules having a low molecular weight, since the method is based on the stabilization due to multi-site bondings. Although some cases are found in which the alternate layer-by-layer method is applied to certain types of dyes or bolaamphiphilic lipids, for stable layering such substances of a low molecular weight must be capable of associating with each other so as to behave in a manner similar to polymer ions.

Thus, the alternate layer-by-layer method cannot always be applied to a variety of low molecular-weight functional molecules. In addition, even when proteins are employed as functional molecules, particularly in layering enzymes such as glucoseoxidase, there may be a cases where no monolayer is formed because of the association of such molecules with each other in an aqueous solution. Improvement is therefore needed in the alternate layer-by-layer method to make it applicable to a wider range of functional molecules by eliminating the above-mentioned problems such as the association of the molecules.

SUMMARY OF THE INVENTION

The present invention is based on the discovery that the above-mentioned problems with respect to the alternate layer-by-layer method can be solved by mixing functional molecules with polymer ions beforehand (premixing) in a solution, and then carrying out alternate layering using the resultant solution.

The present invention thus provides a method for producing a functional thin film which comprises immersing a solid support having an electric charge in a (first) admixed polymer ion-functional molecule solution having a net electric charge opposite to that of the solid support followed by immersing the solid support in a (first) polymer ion solution having a net electric charge opposite to that of the (first) admixed polymer ion-functinal molecule solution, or alternatively immersing a solid support having an electric charge in a (second) polymer ion solution having a net electric charge opposite to that of the solid support followed by immersing the solid support in a (second) admixed polymer ion-functional molecule solution having a net electric charge opposite to that of the (second) polymer ion solution, and repeating such immersing steps of the solid support in the admixed polymer ion solution and the admixed polymer ion-functional molecule solution to form a desired multi-layered thin film.

In another aspect of the present invention, it provides a functional thin film which comprises multiple layers of non-flexible functional molecules and multiple layers of polymer ions fixed on a solid support. Such thin films have not hitherto been producible in any way.

DESCRIPTION OF THE INVENTION

According to the present invention there is provided an ulitrathin film having a thickness of a molecular level, from a variety of molecules, ranging from low molecular weight to high molecular weight molecules, by layering such molecules in the desired number and in the desired order.

The conventional alternate layer-by-layer method is based on the foresaid principle. In the present invention, the adoption of the admixed polymer ion-functional molecule solution, instead of a simple polymer ion solution, makes it possible to layer non-flexible or rigid functional molecules in any desired number and in any desired order of the layers to form an ultrathin film of a molecular level, while such molecules have been difficult to layer in the conventional methods as they are susceptible to association with each other, particularly in the case of proteins.

As can be seen from the above-mentioned principle, according to the present invention the admixed polymer ion-functional molecule solutions can be utilized directly in the preparation of films and hence the decomposition or denaturation of such functional molecules is avoided. Thus, the method for fixing functional molecules according to the present invention provides a remarkable technique for constructing novel functional materials, in marked contrast to the methods hitherto proposed for fixing functional molecules in which chemical modifications of the molecules are needed or denaturation of the molecules occurs and impairs the intrinsic functions of such molecules.

The method of the present invention can be applied to a wide variety of functional molecules since the molecules have only to be mixed with polymer ions to form admixed solutions and need not be modified with specific functional group to develop specific properties for the layering. For example, even materials which are generally difficult to isolate can be easily layered simply by mixing with polymer ions in solutions. In addition, rare materials generally occurring in an extremely small amount can be utilized in the form of admixed solution with polymer ions.

The present invention is also advantageous in that different types of functional molecules can be used in combination and fixed in any desired order so as to construct highly useful composite materials with multiple functions.

In the present invention there are generally employed flexible organic polymer ions as matrices for fixation and thus mass diffusion throughout the thin films is facilitated as compared with the case in which rigid components such as lipids are used as the matrices. It should however be noted that rigid organic or inorganic polymer ions can also be utilized as the fixation matrices in the present invention.

The method of the present invention for preparing thin films can be practiced in an extremely easy manner in a short period of time by simply immersing solid supports into admixed polymer ion-functional molecule solutions, without need of any sophisticated devices. Thus, any types of solid materials can be selected as supports to produce systems imparted with additional functions due to the supports.

The invention will now be described more specifically.

Polymer ions to be used in the present invention can be defined as organic polymers having functional groups with an electric charge on their molecular skeletons or branches, or inorganic polymers with an electric charge. Usable polyanions (anionic polymer ions) are generally ones having such functional groups as sulfonic acid, sulfuric acid and carboxylic acid, which are negatively chargable, and include poly(styrenesulfonate) (PSS), poly(vinylsulfate) (PVS), dextransulfate, chondroitin sulfate, poly(acrylic acid) (PAA), poly(methacrylic acid) (PMA), poly(maleic acid), poly(fumalic acid), and montmorillonite (Mont). Polycations (cationic polymer ions) usable are ones having such functional groups as quaternary ammonium group and amino group, which are positively chargable, and include poly(ethyleneimine) (PEI), poly(allylamine hydrochloride) (PAH), poly(diallyl-dimethyl-ammonium chloride) (PPDDA), poly(vinylpyridine) (PVP) and poly(lysine). These polymer ions are all soluble in water or in a water-organic solvent mixture. Also usable are electrocouductive polymers, functional polymer ions such as those from poly (aniline-N-propane-sulfonic acid) (PAN), and biopolymers such as deoxyribonucleic acid (RNA) and polysaccharide with an electric charge (e.g. pectin). Rigid organic polymer ions such as those deirived from polythiophene, polyaniline and poly(phenylene vinylene) can also be used in the present invention.

All types of functional molecules are applicable in the present invention, so long as such molecules are soluble in a solution together with polymer ions as exemplified above.

Applicable in the present invention are not only such functional molecules as conventionally employed in the alternate layer-by-layer method, but also various types of non-flexible functional molecules which have been hitherto impossible to layer, thereby enabling the construction of a variety of novel functional thin films.

Examples of suitable functional molecules include proteins such as glucose oxydase (GOD; molecular weight 18600, isoelectric point 4.2), peroxydase (POD; molecular weight 42000, isoelectric point 7.2), glucoamylase (GA; molecular weight 100000, isoelectric point 4.2), alcohol dehydrogenase (ADH; molecular weight 100000, isoelectric point 9), diaphorase (DA; molecular weight 700000, isoelectric point 4), cytochrome (Cyt; molecular weight 12400, isoelectiric point 10.1), lysozyme (Lys; molecular weight 14000, isoelectric point 11), histone f3 (His; molecular weight 15300, isoelectric point 11), myoglobin (Mb; molecular weight 17800, isoelectric point 7.0), and hemoglobin (Hb, molecular weight 64000, isoelectric point 6.8), which are suitable for application in catalytic elements and sensors. As applicable functional molecules there are also included such functional pigments or dyes as mordant yellow 10 (MY 10), mordant blue 29 (MB 29), flavin adenine dinucleotide (FAD), Congo Red (CR), tetraphenylporphine-tetrasulfonic acid (TPPS), Acid Red 27 (AR 27), Acid Red 26 (AR 26), Acid Red 52 (AR 52), Bismarck Brown (BB), indigo carmine (IC), and Ponceau S (PS), which may be suitable for application in electroluminescent (EL) elements and other uses. Other functional molecules usable in the present invention, range widely from biopolymers, such as various receptor-proteins, to small molecules.

All types of materials can be utilized as solid supports in the present invention, so long as such materials possess an electric charge on their surfaces (e. g. silver with anionic surface, glass or quartz with anionic surface, and polymer films having a surface charge), or they are capable of being provided with an electric charge, such as gold (capable of being provided with a surface charge due to absorption of a substance such as mercapto-propionic acid) and a variety of electrodes. The fixation or self-assembling according to the present invention is based on the simple adsorption mechanism. It is therefore not indispensable that the supports have a smoothed surface, and a variety of materials can be adopted therefor. For example, porous solid materials such as filters, powdery or particulate materials such as silica gel, and resinous materials in the form of beads, as well as smooth-surfaced solid supports, can be used.

While both the admixed polymer ion-functional molecule solution and the polymer ion solution to be used in the present invention are basically aqueous solutions, they may be mixed solutions with organic solvents depending upon the solubilities of the polymer ions and the functional molecules. The concentrations of the solutions are determined by the solubilities of the functional molecules and the polymer ions in which no strict concentration adjustment is necessary since the absorption steps are based on the neutralization and resaturation of the surface charge. While concentrations may be 5 to 10 mg/ml for a functional molecule and 1 to 3 mg/ml for a polymer ion, they are not restricted to these ranges. If needed, a buffer medium or such a chemical as HCl may be added to control the pH of the solutions and to sufficiently charge the polymer ions.

The method of the present invention for preparing a thin film is generally started with immersing a solid support alternately into two different types of organic polymer ion solutions, in whish one is a solution of polycation and the other is a solution of polyanion, so as to form layers of the flexible polymer ions on the support with the outermost being an organic polymer ion layer with an electrical charge opposite to that of an admixed functional molecule-polymer ion solution.

The thus-precoated support is then (i) immersed into the admixed polymer ion-functional molecule solution, followed by (ii) rinsing, (iii) immersion into a polymer ion solution or into the admixed polymer ion-functional molecule solution and (iv) rinsing. The steps of (i) to (iv) are repeated at desired times so as to produce a multi-layered ultrathin film containing the functional molecules.

In all of the steps, care must be taken to ensure that the net electrical charges of the solutions to be used for adjacent or contiguous layers are opposite to one another. In particular, the poylmer ion used in the admixed polymer ion-functional molecule solution and the polymer ion used in the polymer ion solution are different polymer ions having opposite electric charges. This leads to the construction of a multi-layered thin film of self-assembly in which functional molecule layer is substantially sandwiched between the two different types of polymer ions having the opposite electric charges.

However, the polymer ion used in the admixed polymer ion-functional molecule solution and the polymer ion used in the polymer ion solution may be ones having the same electric charges—not only the same polymer ions having the same electric charges but also different polymer ions having the same electric charge. For example, negatively charged functional molecules are admixed (premixed) with positively charged polymer ions to prepare an admixed polymer ion-functional molecule solution in which the concentration of the polymer ions is relatively low so that the resultant admixed solution has a negative net electric charge, while a polymer ion solution with a positive net charge is prepared from the same polymer ions as used in the admixed polymer ion-functional molecule solution. Thus, immersions of a solid support alternately into such admixed polymer ion-functional molecule solution and polymer ion solution result in the construction of a functional thin film composed of multi layers of the functional molecules and polymer ions.

The formation of the functional thin film of the present invention can be easily verified by appropriate analytical means, among which a quartz oscillator is particularly preferred. The quartz oscillator, known as quartz crystal microbalance (QCM), is a device which, based on change in its frequency, enables determination of the mass or weight of a substance adsorbed thereon with an accuracy of $10^{-9}$ grams. The presence or inclusion of functional molecules in the thin films can be verified by spectroscopic methods, for example, by UV spectral measurements.

The thin films of the present invention can be applied in a reaction system without need for any sophisticated devices. For example, when a thin film of the invention is to be used as an enzymatic element in a liquid reaction system, the solid support with functional layers fixed thereon is simply introduced into a solution containing the substrate for the enzymatic reaction.

The present invention is described in more detail below by way of examples, which in no way limit the invention.

Examples 1–4: Layering and Fixation of MY10 Dye

Examples 1 to 4 illustrate how the present invention improves the alternate layer-by-layer method for constructing functional thin films. In these examples MY10 dye was fixed or assembled on a quartz crystal microbalance having a silver-electrode coating thereon as a solid support to form an ultrathin film. The surface of the silver electrode (surface area: 0.2 cm$^2$) was negatively charged because of partial oxidation. Onto the silver-electrode-coated quartz crystal were alternately fixed several layers of polycation and polyanion as a precursor coating, on which MY10 was adsorbed from an admixed polymer ion-MY10 solution in accordance with the present invention. For comparison, the alternate layering of MY10 and polycation PDDA (Example 1) and also the alternate layering of polyanion PSS and polycation PDDA were also performed in accordance with the conventional method.

Figure 1:
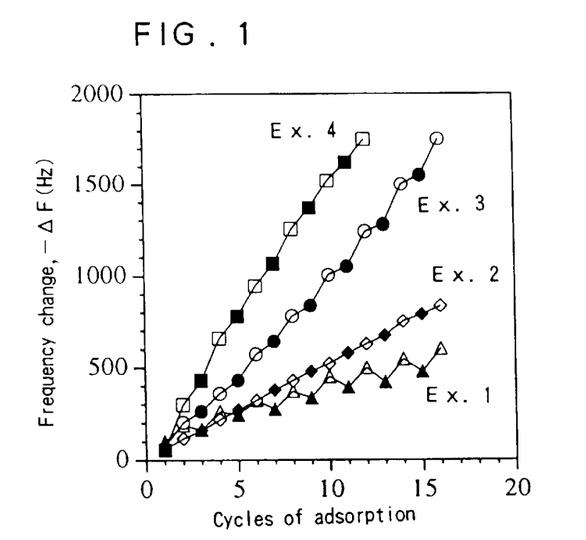
FIG. 1 shows QCM frequency changes observed in the alternate layer-by-layer assembling of Examples 1 to 4.

FIG. 1 shows the QCM frequency changes observed in these Examples. As can be seen from the result in Example 2 (for comparison), alternate layering of the oppositely charged polymer ions produced a regularly increasing frequency change, suggesting regular growth of the film.

However, in the case of Example 1 (for comparison) where MY10, a low molecular weight molecule, was employed together with the polymer ion, alternate increase and decrease in the film mass was observed, suggesting that the construction of an ultrathin film composed of MY10 is not feasible by the conventional alternate layer-by-layer method.

In Example 3 in accordance with the present invention, MY10 and PSS were premixed in a ratio of [MY10]/[PSS]=1 mM/15 mM to form an admixed solution, followed by alternate layering by immersing the precursor-coated support alternately in the admixed solution and a PDDA solution.

In Example 4 in accordance with the present invention, MY10 and PSS were admixed or premixed in a ratio of [MY10]/[PSS]=10 mM/15 mM to form an admixed solution, followed by alternate layering by immersing the precursor-coated support alternately in the admixed solution and the PDDA solution. FIG. 1 also gives the frequency changes for these adsorption procedures, all of which demonstrate highly regular growth of the film. As the film growth rates in Examples 3 and 4 were clearly higher than that in Example 2 employing PSS and PDDA, it is clear that MY10 is included in the films in Examples 3 and 4. It is also observed that the film growth rate in Example 4 was higher than in Example 3, suggesting that the higher is the proportion of MY10 in the admixed solution, the higher is the film growth rate. This also verifies that the increased growth rate of film in Examples 3 and 4 is based on the higher amount of MY10 adsorption. These results thus demonstrate that the admixing of MY10 dye with PSS prior to alternate layer-by-layer assembling step enables the growth of the films with regularly-layered structures, which have never been producible by the conventional alternate layer-by-layer method.

Examples 5 & 6: Studies on Ionic Strength and Dielectric Coefficient

Figure 2:
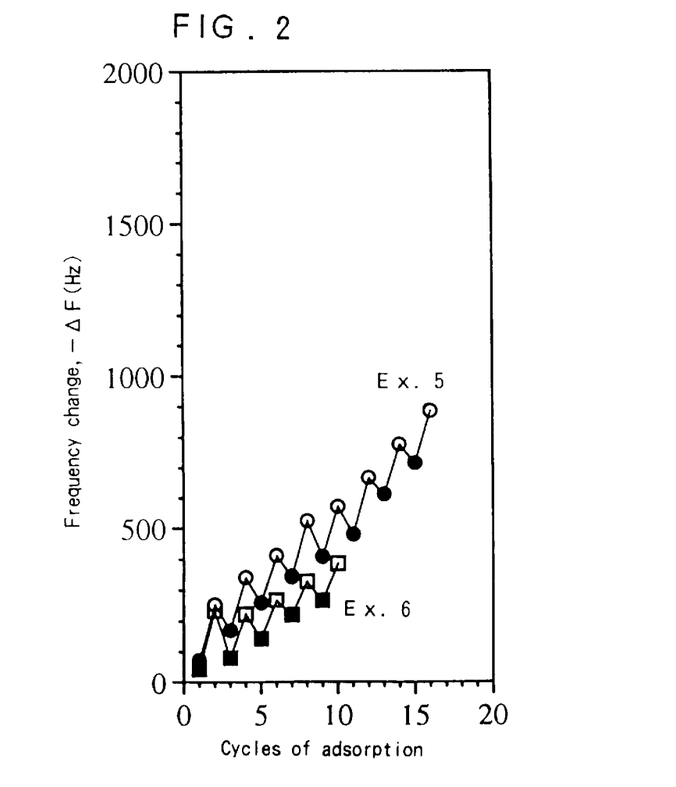
FIG. 2 shows QCM frequency changes observed in the alternate layer-by-layer assembling of Examples 3 and 4.

In Example 5, alternate layer-by-layer assembling was attempted by immersing the solid support alternately in an aqueous MY10 solution and in an aqueous PDDA solution both containing 1M NaCl. Alternate layer-by-layer assembling was also attempted, in Example 6, by the alternate immersion of the support in an aqueous MY10 solution and in an aqueous PDDA solution both containing 50% acetone. FIG. 2 shows QCM frequency changes for these examples, in which there are observed alternate increase and decrease in the film mass, suggesting that no efficient film growth was achieved. It is thus verified that the simple change in ionic strength or dielectric constant in the solution will not produce any improvement over the conventional method.

Examples 7 through 10: Verification of Inclusion of MY10

Figure 3:
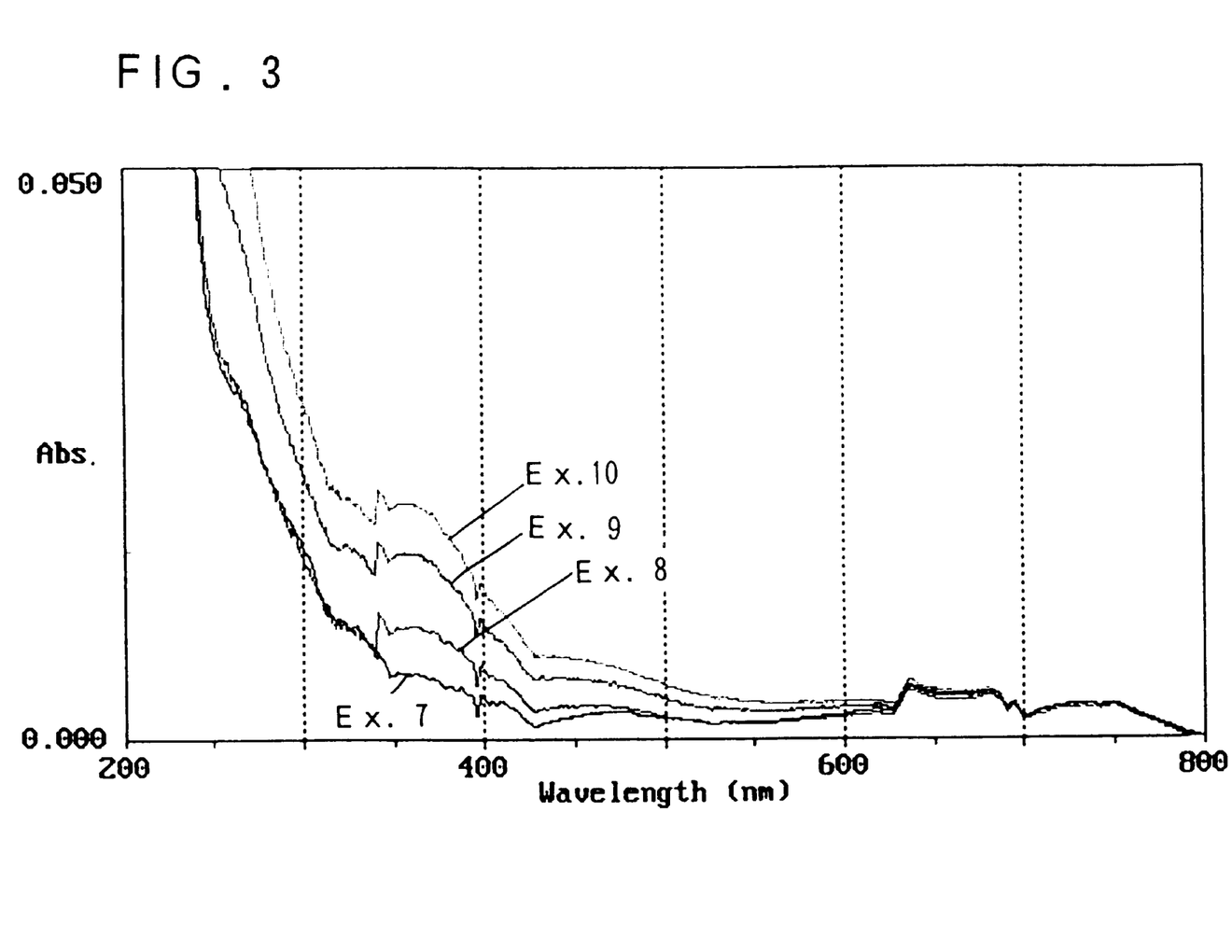
FIG. 3 shows UV spectra observed in Examples 8 to 10.

These examples are to verify that MY10 molecules are actually included or present in the films of a layered structure obtained by the method of the present invention. As in aforementioned Example 4, admixed MY10/PSS solution ([MY10]/[PSS]=10 mM/15 mM) was prepared for an alternate layer-by-layer assembling by immersing the solid support alternately in the admixed solution and in PDDA solution. Alternate-layered films differing in the number of layers were prepared for UV spectral measurement. FIG. 3 illustrates the spectra of the films having 0, 1, 5 and 10 layers of MY10, designated as Examples 7, 8, 9 and 10, respectively. Absorption peaks are observed at around 350 nm in the spectra of the films having the dye layer(s) as expected, indicating the fixation of MY10 molecules within the films. It was also found that the peak intensity increases with increasing number of the layers.

Thus, the results verify, together with the QCM data shown in FIG. 1, that the method of the invention is effective in the growth of the films.

Examples 11–20: Layering and Fixation of Various Dye Molecules

These examples illustrate the applicability of the present invention to a variety of dye molecules. Different types of dye molecules were layered by alternate layer-by-layer methods to make a quantitative study of film growth by means of the quartz crystal microbalance. The results are expressed in terms of average frequency changes for the respective dyes, as given in Table 1.

Examples 11, 12, 16 and 18 are films in which PSS and PDDA, MY10 and PDDA, FAD and PDDA, and MB29 and PDDA were respectively layered by the conventional alternate layer-by-layer technique. Except for Example 11 in which two different polymer ions were employed for the alternate layering, a decrease or only a slight increase in the film mass was observed in each step of cation adsorption and/or anion adsorption, suggesting the inapplicability of the conventional alternate technique to MY10, FAD or MB29.

By contrast, in the cases of Examples 13 and 14 in which admixed MY10-PSS solution was employed, Example 17 in which admixed FAD-PSS solution was employed and Example 20 in which admixed MB29-PDDA solution was employed in accordance with the present invention, a clear increase in the film mass indicative of film growth is observed in each step of anion adsorption and cation adsorption. The frequency changes in these Examples were higher than those in the alternate layering of PSS and PDDA, indicating that the dye molecules were effectively fixed within the films.

The results thus demonstrate that a variety of dye molecules, such as those which have been difficult to layer to form a film by the conventional layer-by-layer method, can be successful layered and assembled by premixing such dyes with polymer ions according to the present invention. There may be cases in which sufficient film growth is not obtained as in Example 15 with admixed MY10/PDDA and Example 19 with MB29/PSS. This suggests that the respective dyes should be admixed with the corresponding appropriate, compatible polymer ions.

TABLE 1

| | Anion Component | Frequency Change(Hz) | Cation Component | Frequency Change(Hz) |
|---|---|---|---|---|
| Example 11 | 15 m M P S S | 53 | 19 m M P D D A | 50 |
| Example 12 | 1 m M M Y 10 | 105 | 1.9 m M P D D A | −48 |
| Example 13 | 1 m M M Y 10/15 m M P S S | 163 | 19 m M P D D A | 55 |
| Example 14 | 10 m M M Y 10/15 m M P S S | 188 | 19 m M P D D A | 133 |
| Example 15 | 15 m M P S S | 214 | 10 m M M Y 10/19 m M P D D A | 7 |
| Example 16 | 1 m M F A D | 156 | 1.9 m M P D D A | −32 |

TABLE 1-continued

| | Anion Component | Frequency Change(Hz) | Cation Component | Frequency Change(Hz) |
|---|---|---|---|---|
| Example 17 | 10 m M F A D/15 m M P S S | 117 | 19 m M P D D A | 29 |
| Example 18 | 1 m M M B 29 | −2 | 1.9 m M P D D A | 10 |
| Example 19 | 10 m M M B 29/15 m M P S S | 214 | 19 m M P D D A | 34 |
| Example 20 | 15 m M P S S | 83 | 10 m M M B 29/19 m M P D D A | 75 |

TABLE 2

| | Anion Component | Frequency Change(Hz) | Cation Component | Frequency Change(Hz) |
|---|---|---|---|---|
| Example 21 | 1 mg/mL G O D | 2330 | 1 mg/mL P E I | 52 |
| Example 22 | 0.5 mg/mL G O D | 2125 | 1 mg/mL P E I | 50 |
| Example 23 | 0.005 mg/mL G O D | 670 | 1 mg/mL P E I | 44 |
| Example 24 | 0.5 mg/mL G O D/1 mg/mL P S S | 482 | 1 mg/mL P E I | 45 |
| Example 25 | 0.05 mg/mL G O D/1 mg/mL P S S | 468 | 1 mg/mL P E I | 33 |
| Example 26 | 1 mg/mL P S S | 130 | 0.5 mg/mL G O D / 1 mg/mL P E I | 382 |
| Example 27 | 1 mg/mL P S S | 149 | 0.05 mg/mL G O D / 1 mg/mL P E I | 185 |
| Example 28 | 1 mg/mL P S S | 110 | 1 mg/mL P E I | 40 |

Examples 21–28: Layering and Fixation of Proteins

The Examples 21–28 were carried out to study the applicability of the present invention for constructing films composed of proteins. The results are summarized in Table 2.

Examples 21 and 22 are given for films prepared by the conventional alternate layer-by-layer method, in which GOD enzyme was layered alternately with PEI. In these Examples there is observed a very large frequency change in each adsorption step, which corresponds to a simultaneous layering of 3 to 4 GOD layers, suggesting that the GOD was assembled in the form of multi-layered and associated molecules.

By contrast, with Examples 23 and 24 in which an admixed GOD/PSS solution was employed for the alternate layering with PEI and also with Examples 25 and 26 in which an admixed GOD/PEI solution was employed for the alternate layering with PSS, the frequency changes resulting from the GOD adsorption were found to be relatively small. At the same time, such frequency changes are significantly larger than those in Example 27 and 28 in which the alternate layering was conducted using PSS and PEI. Thus, it was verified that in the films of Examples 23 through 26 GOD molecules are layered and fixed without occurrence of the association of molecules, by premixing (admixing) GOD with polymer ions.

Examples 29–34: Enzyme Reaction Using the Thin Films

Examples 29–34 are to illustrate enzyme reactions carried out by immersing the films obtained as in the above-described Examples 21–27 in an aqueous solution containing glucose, POD and DA67 (a redox enzyme). As the reaction proceeded, DA67 was oxidized, resulting in an increased absorption at 665 nm. This spectral change with time is an indication of the enzyme activity. Thus, the relative enzyme activities per unit weight of the enzyme were determined for the respective cases, in which the enzyme activity of the film in Example 29 was employed as a standard. The results are given in Table 3.

TABLE 3

| | Film employed | Relative Activity |
|---|---|---|
| Example 29 | Example 21 | 1.000 |
| Example 30 | Example 22 | 0.998 |
| Example 31 | Example 23 | 0.995 |
| Example 32 | Example 24 | 1.958 |
| Example 33 | Example 25 | 7.407 |
| Example 34 | Example 26 | 7.284 |
| Example 35 | Example 27 | 67.44 |

In Examples 29 and 30 were used the films prepared by the conventional alternate layer-by-layer method, in which the film in Example 30 was prepared from a solution with a smaller GOD concentration as compared with the film in Example 29. There are observed no enhancement in the relative activity with Example 30. It is clearly indicated that the employment of an admixed solution will result in an enhancement in the enzyme activity, as seen in Examples 23 and 24 in which GOD/PSS admixed solutions were used in the alternate layer-by-layer assembling with PEI and also in Examples 25 and 26 in which GOD/PEI admixed solutions were used in the alternate layer-by-layer assembling with PSS.

It was also found that GOD of a smaller concentration admixed with the polymer ions produced a higher enzyme activity as can be seen from the comparison between Examples 31 and 32 and that between Examples 33 and 34. This fact may be reasoned that the less is the GOD proportion in the admixture, the more effectively the association of GOD molecules are suppressed and the diffusion of the substrate is facilitated resulting in the enhancement in the enzyme activity. It was further noted that the admixing of the enzyme with oppositely charged polymer ions in a solution led to a higher relative activity, as can be seen from a comparison between Examples 31 and 33 and also that between Examples 32 and 34. Thus, it was shown that admixing of an enzyme with a polymer ion which will exert a stronger interaction with the enzyme results in an increased activity due to the suppression of the association of the enzyme molecules.

Examples 35–37

Figure 4:
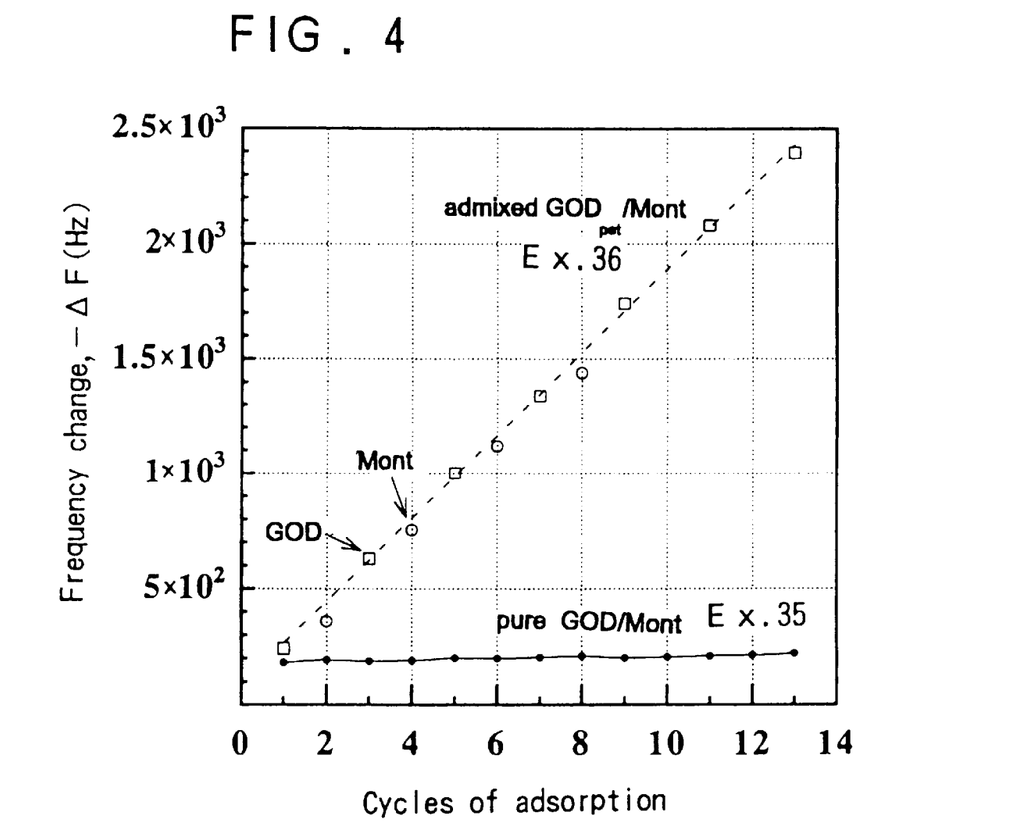
FIG. 4 shows QCM frequency changes observed in the alternate layer-by-layer assembling of Examples 35 and 36.

The alternate layer-by-layer assembling on quartz crystal was carried out by immersing the precoated quartz crystal microbalance alternately in an admixed GOD/PEI solution ([GOD]):[PEI]=0.5 mg/ml: 1 mg/ml] and a Mont solution (0.3 mg/ml) for Example 35, and alternately in a GOD solution (0.5 mg/ml) and a Mont solutions (0.3 mg/ml) for Example 36. The resultant frequency changes are shown in FIG. 4. No film growth is observed in Example 36. This is probably because both GOD and Mont were negatively charged and no adsorption due to the electrostatic interaction occurred. By contrast, in Example 35 the oppositely charged polymer ions and GOD molecules were premixed to form an admixed solution with a positive net charge, which enabled the alternate adsorptions with the negatively charged Mont.

Figure 5:
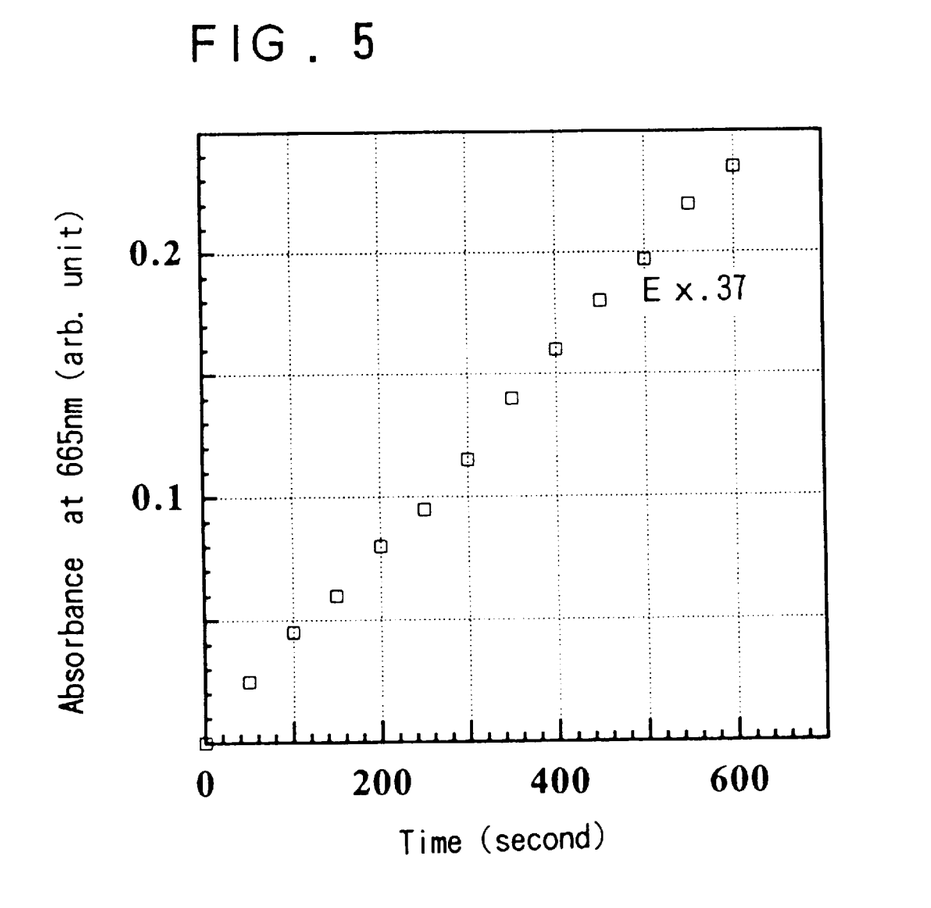
FIG. 5 shows an increase in UV absorbance at 665 nm observed in Example 37.

This example also verifies that PEI, a flexible molecule present in the admixture, allowed the alternate layering of GOD with Mont (rigid or non-flexible molecules). Measurements were also conducted, for Example 37, of UV absorption at 665 nm on the film employed in Example 35. FIG. 5 shows that a regular increase in the UV absorption is observed with time, indicating a steady layering or self-assembly of GOD molecules. The subject examples thus demonstrate that the present invention of has enabled the alternate layer-by-layer assembling of likely charged materials as well as a hybrid-type alternate layering of an organic material and an inorganic material.

Figure 6:
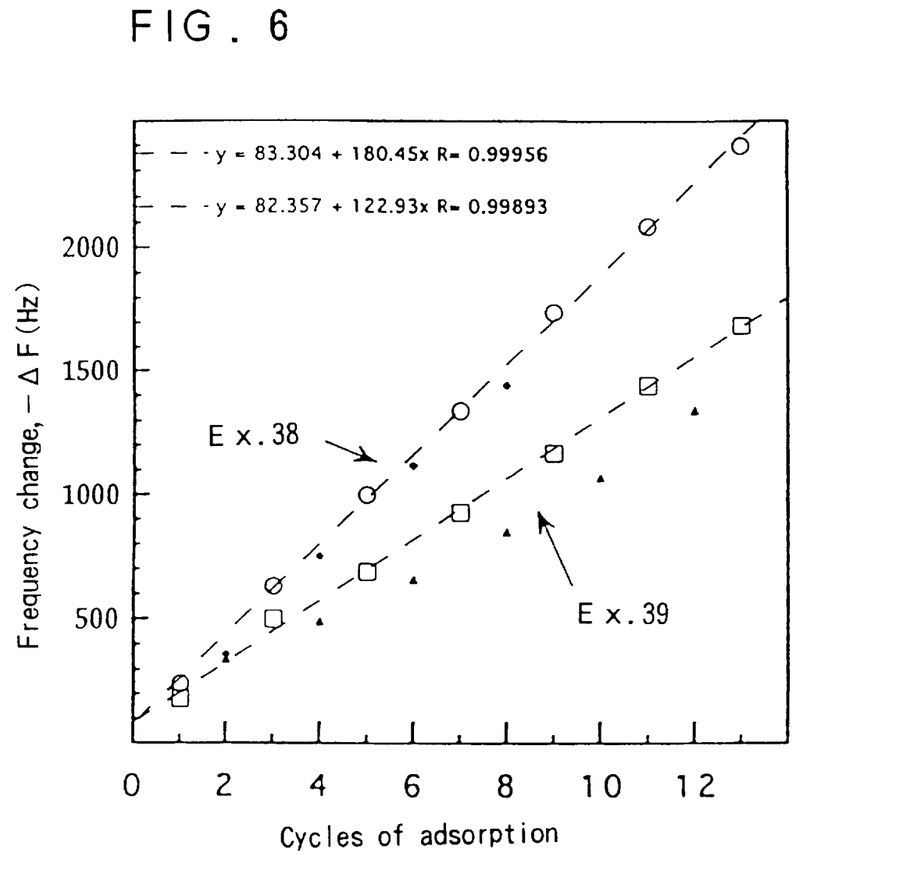
FIG. 6 shows QCM frequency changes observed in the alternate layer-by-layer assembling of Examples 38 and 39.

Examples 38–41: Alternate Layer-by-layer Assembly of Plural Non-flexible Materials In Example 38 a GOD/PEI admixture (GOD:0.5 mg/ml, PEI:1 mg/ml) was prepared for alternate layer-by-layer assembly with Mont on the precoated quartz crystal microbalance. The resultant frequency changes are given in FIG. 6, from which it is indicated that alternate GOD layers and Mont layers are successfully formed. Hitherto it has been impossible to perform an alternate layer-by-layer assembling with GOD and Mont as both substances are rigid or inflexible. According to the present invention the premixing of GOD with PEI allows the alternate layer-by-layer assembling of such two rigid substances in which PEI presumably serve as a glue.

In Example 39, GOD (0.5 mg/ml) and PEI (1 mg/ml) are premixed for an alternate layer-by-layer assembling with PSS on the quartz crystal microbatance. The resultant frequency changes are also given in FIG. 6, from which it is indicated that alternate GOD layers and PSS layers are successfully formed. It has hitherto been impossible to conduct an alternate layer-by-layer assembling with GOD and PSS as these substances are likely charged. The premixing of GOD with PEI possibly result in the conversion of negative charge of GOD into a positive net charge, thus allowing the alternate layer-by-layer assembling with PSS, a polyanion.

Figure 7:
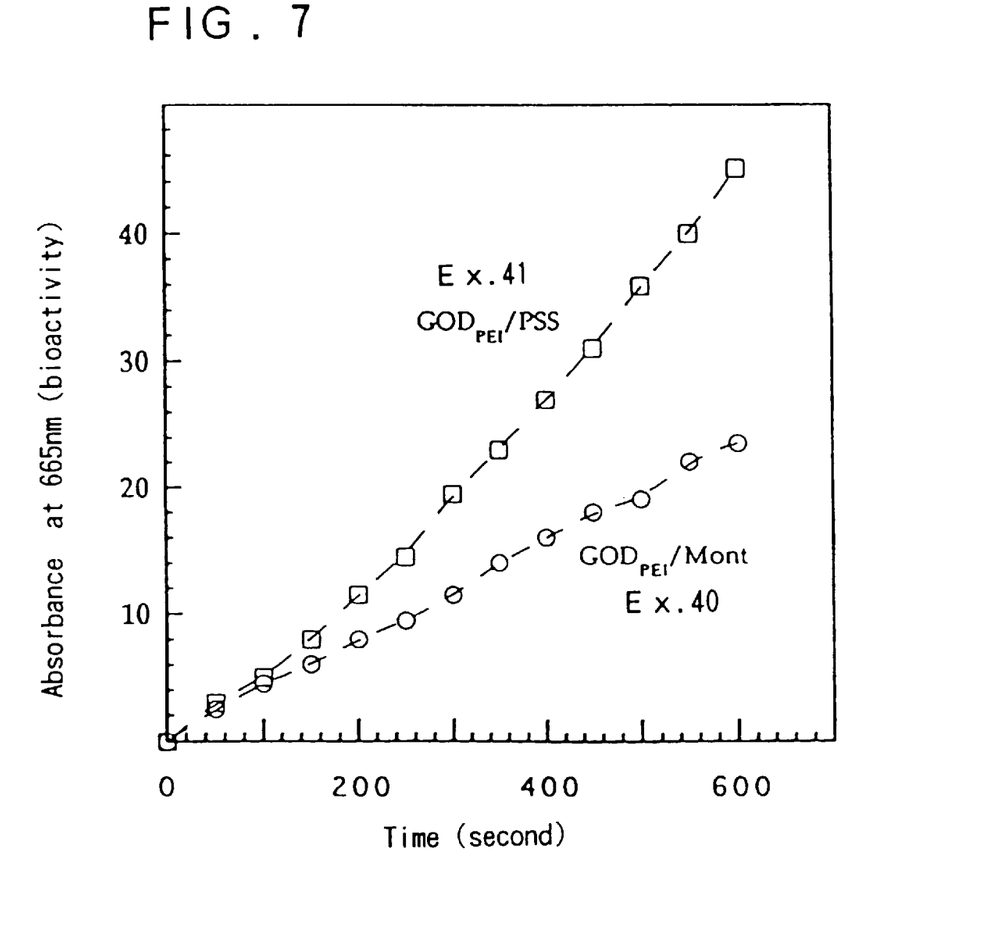
FIG. 7 shows UV spectra observed in Examples 40 and 41.

In Example 40 and Example 41, enzymatic activity of GOD was determined by immersing the film obtained in Example 38 and Example 39 respectively in solutions containing glucose, POD and DA67 and measuring absorbance at 665 nm. The results are given in FIG. 7, from which it is seen that the absorbance in creases as time lapses, demonstrating the enzymatic activity of GOD is effectively maintained within the film assemblies.

Figure 8:
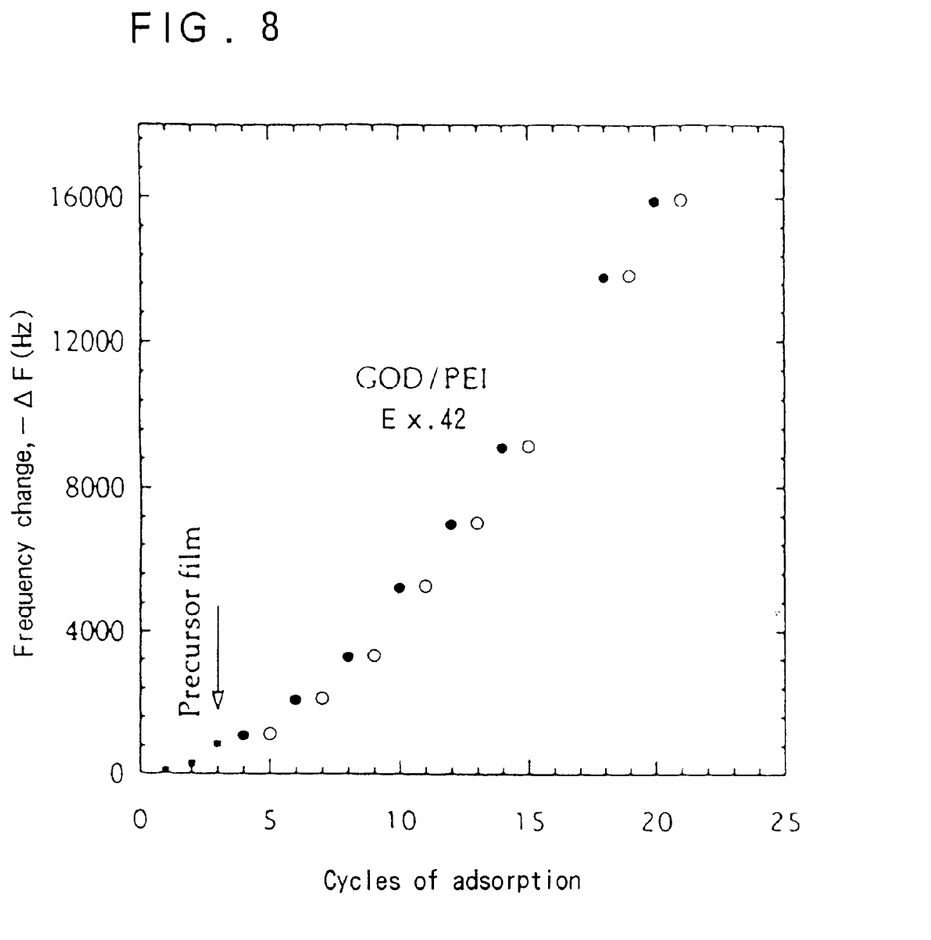
FIG. 8 shows QCM frequency changes observed in the alternate layer-by-layer assembling of Example 42.

Example 42: Alternate Layer-by-layer Assembly Composed of Different Polymer Ions of Like Charges In Example 42, an admixed GOD/PEI solution (GOD:0.5 mg/ml, PEI:0.01 mg/ml) was prepared for an alternate layer-by-layer assembling with PEI on the quartz crystal microbalance. The resultant frequency changes are given in FIG. 8, from which it is seen that the alternate GOD layers and PEI layers were successfully formed. In this example, the electric charges of the admixed solution was dominated by the negatively charged GOD as the PEI concentration was adjusted to be relatively low, thereby enabling the alternate layering with the positively charged PEI. The premixing in accordance with the present invention thus makes it possible to obtain a solution of a functional molecule having any desired net electric charge, either positive or negative, by adjusting concentration of the functional molecule relative to that of an organic polymer ion in the solution. This leads to versatile selection of a substance or material with which the functional molecule is employed for an alternate layer-by-layer assembly.

As detailed in the above, according to the present invention functional molecules are premixed or admixed with polymer ions in a solution for an alternate layer-by-layer assembling process, thereby successfully constructing functional films composed of a variety of non-flexible functional molecules such as those which have been difficult to assemble by the conventional alternate layer-by-layer method. For example, a film composed of layers of dye molecules having a low molecular weight can be formed. It is also possible to construct, from an enzyme/polymer ion admixture, a layered-structure in which the association of the enzyme molecules are suppressed to exhibit an increased enzyme activity. Additionally, the premixing with polymer ions makes it possible to convert the net electric charge of functional molecules, thereby enabling an alternate layer-by-layer assembling with a substance having the same electrical charge as the functional molecules, such alternate layering being intrinsically impossible by the conventional method. Furthermore, according to the present invention there can be obtained an alternate layer-by-layer assembly made up of two or more different types of rigid molecules in a film, by the premixing with flexible polymer ions, such assembly having been impossible to obtain by the conventional method. The films of the present invention are composed of a layered-structure of a variety of functional molecules ranging from low molecular weight molecules to polymer molecules, providing good prospects of developing such devices as molecular devices and artificial reactors of the new generation.

What is claimed is:

1. A method for producing a multiple layered functional thin film which comprises:

immersing a solid support having an electric charge in a solution containing a mixture of functional molecules that provide a desired function in a physical or chemical process and charged polymer molecules, different from the functional molecules, that form a matrix to fix the functional molecules, which solution of functional molecules and charged polymer molecules having a net electric charge opposite to that of the solid support, to form a layer containing said functional molecules and said charged polymer molecules;

immersing the solid support and said layer containing said functional molecules and said charged polymer molecules in a solution containing charged polymer molecules having a net electric charge opposite to that of said solution containing the mixture of charged polymer molecules and functional molecules; and repeating at least once said steps of immersing said solid support in a solution containing a mixture of charged polymer molecules and functional molecules and in a solution containing charged polymer molecules to form a desired multi-layered thin film.

2. The method of claim 1, wherein the charged polymer molecules used in said solution containing a mixture of charged polymer molecules and functional molecules and the charged polymer molecules used in said solution containing charged polymer molecules are different charged polymer molecules having opposite electric charges.

3. The method of claim 1, wherein the charged polymer molecules used in said solution containing a mixture of charged polymer molecules and functional molecules and the charged polymer molecules used in said solution containing charged polymer molecules are charged polymer molecules having the same electric charge.

4. A multiple layered functional thin film produced by the method of claim 1.

5. The multiple layered functional thin film of claim 4, wherein the functional molecules are proteins.

6. The multiple layered functional thin film of claim 5, wherein the protein is selected from the group consisting of glucose oxidase, peroxidase, glucoamylase, alcohol dehydrogenase, diaporase, cytochrome, lysozyme, histone, myoglobin, and hemoglobin.

7. The multiple layered functional thin film of claim 4, wherein the functional molecules are pigments or dyes.

8. The multiple layered functional thin film of claim 7, wherein the pigment is selected from the group consisting of mordant yellow, mordant blue, flavin adenine dinucleotide, Congo Red, tetraphenylporphine-tetrasulfonic acid, Acid Red 27, Acid Red 26, Acid Red 52, Bismarck Brown, indigo carmine, and Ponceau.

9. The multiple layered functional thin film of claim 4, wherein as the charged polymer molecules are employed two different charged polymer molecules having opposite electrical charges.

10. The multiple layered functional thin film of claim 4, wherein the charged polymer molecules used in at least one of the solution containing charged polymer molecules and functional molecules and the solution containing charged polymer molecules are anionic polymer ions which include a functional group selected from the group consisting of sulfonates, sulfates, and carboxylates.

11. The multiple layered functional thin film of claim 4, wherein the charged polymer molecules used in at least one of the solution containing charged polymer molecules and functional molecules and the solution containing charged polymer molecules are cationic polymer ions having a functional group selected from the group consisting of quaternary ammonium ions and amines.

12. The multiple layered functional thin film of claim 4, wherein the charged polymer molecules are soluble in one of water and a water-organic solvent mixture.

13. A method for producing a multiple layered functional thin film which comprises:

immersing a solid support having an electric charge in a solution containing charged polymer molecules having a net electric charge opposite to that of the solid support to form a layer containing said charged polymer molecules;

immersing the solid support and said layer containing said charged polymer molecules in a solution containing a mixture of functional molecules that provide a desired function in a physical or chemical process and charged polymer molecules, different from the functional molecules, that form a matrix to fix the functional molecules, which solution of functional molecules and charged polymer molecules having a net electric charge opposite to that of the solution containing the charged polymer molecules;

repeating at least once said steps of immersing of said solid support in a solution containing charged polymer molecules and in a solution containing a mixture of charged polymer molecules and functional molecules to form a desired multi-layered thin film.

14. The method of claim 13, wherein the charged polymer molecules used in said solution containing a mixture of charged polymer molecules and functional molecules and the charged polymer molecules used in said solution containing charged polymer molecules are different charged polymer molecules having opposite electric charges.

15. The method of claim 13, wherein the charged polymer molecules used in said solution containing a mixture of charged polymer molecules and functional molecules and the charged polymer molecules used in said solution containing charged polymer molecules are charged polymer molecules having the same electric charge.

16. A multiple layered functional thin film produced by the method of claim 13.

17. The multiple layered functional thin film of claim 16, wherein the functional molecules are proteins.

18. The multiple layered functional thin film of claim 17, wherein the protein is selected from the group consisting of glucose oxidase, peroxidase, glucoamylase, alcohol dehydrogenase, diaporase, cytochrome, lysozyme, histone, myoglobin, and hemoglobin.

19. The multiple layered functional thin film of claim 16, wherein the functional molecules are pigments or dyes.

20. The multiple layered functional thin film of claim 19, wherein the pigment is selected from the group consisting of mordant yellow, mordant blue, flavin adenine dinucleotide, Congo Red, tetraphenylporphine-tetrasulfonic acid, Acid Red 27, Acid Red 26, Acid Red 52, Bismarck Brown, indigo carmine, and Ponceau.

21. The multiple layered functional thin film of claim 16, wherein as the charged polymer molecules are employed two different charged polymer molecules having opposite electrical charges.

22. The multiple layered functional thin film of claim 16, wherein the charged polymer molecules used in at least one of the solution containing charged polymer molecules and functional molecules and the solution containing charged polymer molecules are anionic polymer ions which include a functional group selected from the group consisting of sulfonates, sulfates, and carboxylates.

23. The multiple layered functional thin film of claim 16, wherein the charged polymer molecules used in at least one of the solution containing charged polymer molecules and functional molecules and the solution containing charged polymer molecules are cationic polymer ions having a functional group selected from the group consisting of quaternary ammonium ions and amines.

24. The multiple layered functional thin film of claim 16, wherein the charged polymer molecules are soluble in one of water and a water-organic solvent mixture.

* * * * *